United States Patent [19]

Felsch et al.

[11] 4,247,702

[45] Jan. 27, 1981

[54] METHOD OF STABILIZING 4-METHYL-5-(2'CHLOROETHYL)-THIAZOL

[75] Inventors: Horst Felsch, Fieberbrunn; Gerhard Hantich, Kitzbühel, both of Austria

[73] Assignee: Pharmaceutical Licences Company Ltd., Prangins, Switzerland

[21] Appl. No.: 28,914

[22] Filed: Apr. 10, 1979

[30] Foreign Application Priority Data

Apr. 25, 1978 [AT] Austria ............................ 2961/78

[51] Int. Cl.$^3$ ............................................. C07D 277/20
[52] U.S. Cl. ................................... 548/146; 424/270
[58] Field of Search ................. 260/302 R; 548/146

[56] References Cited

FOREIGN PATENT DOCUMENTS 266126 11/1968 Austria .
2206943 6/1974 France .

*Primary Examiner*—Nicholas S. Rizzo
*Attorney, Agent, or Firm*—Mason, Fenwick & Lawrence

[57] ABSTRACT

Stabilization method for 4-methyl-5-(2'-chloroethyl)-thiazol, where the latter is mixed with a nontoxic carrier substance which contains at least one triglyceride of at least one saturated fatty acid with a chain length of $C_8$ to $C_{12}$, preferably an oil.

5 Claims, No Drawings

METHOD OF STABILIZING 4-METHYL-5-(2'CHLOROETHYL)-THIAZOL

This invention relates to a method for stabilizing 4-Methyl-5-(2'-Chlorethyl)-thiazol, in which the latter is mixed with a nontoxic carrier substance which contains at least one glyceride, preferably an oil. It is known that 4-Methyl-5-(2'-Chlorethyl)-thiazol having the following formula

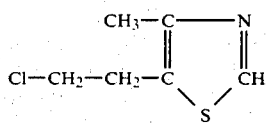

(hereafter abbreviated as CMT) has a sedative and anti-convulsive effect. But in terms of its chemical structure, the CMT-Base is unstable. It was discovered earlier (Austrian Pat. No. 266,126) that, especially in case of longer storage and at higher temperatures, decomposition reactions develop, specifically, a separation of HCl. The developing decomposition products no longer have the same pharmacological effects as the CMT-Base.

A further disadvantage consists in the fact that CMT usually—especially in case of infusion solutions and injection solutions—is used in the form of an ethane disulfonate. For peroral forms, this however introduces the disadvantage of an unpleasant taste and odor which comes from smaller quantities of free base and which so far could be hardly masked successfully.

To eliminate these disadvantages, it has already been proposed (Austrian Pat. No. 266,126) that CMT be mixed with a nonpolar, nontoxic carrier which consist of one or several animal or vegetable oils or fats, especially peanut oil, or which is made up of one or more higher fatty acids, whereby the latter are compounds with 14 to 22 carbon atoms. In this way one can slow down the decomposition of the CMT-Base so that the preparations obtained can be stored for some time. The unpleasant, sulfurous odor and the bitter taste however remain with these preparations.

Moreover, investigations conducted by the patent holder showed that, in addition to the initially mentioned HCl separation, there are other reactions which lead to the decomposition of the CMT-Base. If freshly distilled CMT-Base is kept for several days at higher temperature and if the decomposition products, in the form of the precipitated brown deposit, are washed with benzene and analyzed, one finds that the quantity of the total chloride obtained by such analyses is essentially greater than the sum of the free chloride and the chloride derived from CMT-Base and the CMT-HCl occluded by the decomposition products. In other words, an excess of chloride accordingly must be bound to the decomposition products of the CMT-Base.

The purpose of the invention is an improved method of the kind described initially wherein the stability of the base will be so increased that preparations will remain preserved during storage at room temperature, for at least four years and moreover, will be tasteless and odorless. The invention solves this problem essentially by using, as a carrier substance, at least a semi-synthetic or fully-synthetic triglyceride on a base of saturated average fatty acids (that is to say, fatty acids with chain length $C_8$ to $C_{12}$).

As said before, it has developed that, in addition to the HCl separation in a mixture of CMT-Base and a carrier substance, the latter is vulnerable to autoxydation reactions if the carrier substance contains reactive groups, such as, for example, free acids or alcohol components or olefinic double compounds, as is the case with vegetable and animal oils or fats. In addition to HCl separation, there are radical decomposition mechanisms possible in the CMT-Base based on autoxydation reactions. This decomposition, which can occur in addition to the HCl separation, is all the more likely, the more the selected carrier substance is susceptible to autoxydation reactions. This is why, in accordance with this invention, a physiologically unobjectionable carrier substance is selected which, in addition to providing a stabilizing effect against HCl separation, will not be sensitive to oxygen in the air and which therefore will not induce any decomposition of the CMT-Base through autoxydation reactions. Carrier substances, which contain animal or vegetable oils or fats, therefore cannot be considered here because they are extraordinarily prone to autoxydation because of their content of unsaturated fatty acids. By means of subsequent measures, for example, hydration, the content of unsaturation can be reduced but not to the extent that the autoxydation capability would be decisively reduced.

Triglycerides of the kind according to the invention, as well as their mixtures, are physiologically unobjectionable because they are decomposed according to the fatty acid cycle. Such triglycerides or triglyceride mixtures based on saturated fatty acids with average chain length ($C_8$ to $C_{12}$) can easily be made synthetically by means of esterification of glycerine with fatty acids, for example, as saturated n-alkanic acids of average chain length with an even-numbered carbon chain (saturated vegetable or animal fatty acids of average chain length). The fatty acids used can be obtained synthetically or by saponification of natural fats or oils, hydration and purification. Such triglycerides or triglyceride mixtures do not contain any double bonds (the iodine number is smaller than 1) and they are very stable. The use of glycerine as alcohol component and saturated n-alkanic acids of average chain length, with an even-numbered carbon number as acid component, can be explained in the light of the need for good physiological tolerability.

In one preferred version of the method according to the invention, there is used as the carrier substance, a double-bond-free triglyceride of a mixture of saturated fatty acids with an average chain length of $C_8$ to $C_{12}$, especially with an even number of carbon atoms, whose iodine number is smaller than 1, preferably a low in heavy metal ion content neutral oil. Such triglyceride mixtures are very stable. Known triglyceride of mixed saturated vegetable fatty acids with a chain length of $C_8$ to $C_{12}$ have a content of $C_6$ chain lengths amounting to a maximum of 3%, which can be neglected. Their iodine number is below 1 and the heavy metal trace value is below 0.001%. The acid number is below 0.1. These data are particularly favorable in terms of insensitivity to autoxydation.

Experiments conducted by the patent owner furthermore showed that the previously mentioned autoxydation can be reduced, or, avoided not only by means of suitable selection of the carrier substance but also by means of carrying out, within the context of the invention, the mixing of 4-methye-5-(2'-chlorethyl)-thiazol with the carrier substance, in the absence of aerial oxygen, preferably in an inert gas atmosphere, especially a nitrogen atmosphere. Preferably according to the invention, the mixture obtained is further kept in soft gelatin capsules under an inert gas atmosphere, especially a nitrogen atmosphere, to preclude contact of the capsule contents with an air bubble until emptied. If necessary, however, one could use other inert gases, such as krypton, argon or neon; but nitrogen is best for reasons of price.

Mixing and storage as an inert gas atmosphere prevents or reduces decomposition reactions which are induced or speeded up by the presence of air oxygen. As said before, such autoxydation reactions are accelerated mostly by the presence of reactive groups (for example, olefinic double bonds, free acids) or by heavy metal ions. Since in the invention, on the one hand, the carrier substance has been so selected that, with a view of such reactions, it will behave in the most neutral or inert manner possible (particularly when it has an iodine number of less than 1, an acid number of less than 0.1, and heavy metal ion traces smaller than 0.001%), and because, on the other hand, the entry of air oxygen is being avoided both in the mixture and in the subsequent storage and emptying of the mixture, it is found that autoxydation reactions are so reduced that the mixture obtained can be stored over several years. The air-bubble-free loading of the mixture of CMT-Base and carrier substance in soft gelatin capsules is easily possible for example according to the Scherer method. It is a good idea to have the soft gelatin capsules contain softening agents such as sorbite or glycerin to prevent them from becoming brittle. Particularly good density, also with respect to odor density, in these gelatin capsules could be obtained by means of a glycerin content of 10–20% by weight and a sorbite content of 10–20% by weight.

Among the triglyceride mixtures, which are particularly suitable within the context of this invention, those which have the following fatty acid distribution are particularly suitable.

| Caproic Acid | ($C_6$) | 3% max. | 3% max. | 3% max. |
|---|---|---|---|---|
| Caprylic acid | ($C_8$) | 65–80% | 50–65% | 65–80% |
| Capric acid | ($C_{10}$) | 15–30% | 30–45% | 15–30% |
| Lauric acid | ($C_{12}$) | 3% max. | 5% max. | 3% max. |
| Linoleic acid | ($C_{18}$) | — | — | — |

Experiments conducted by applicant showed that one can use, as carrier substance, in addition to these compounds, also glyceryltricaprinate or glyceryltrilaurate.

If a controlled release of the active substance in the intestinal tract is desired for special pharmaceutical uses, then it is a advantageous to coat the capsule with stomach-juice-resistant, intestine-soluble, i.e. enteric coatings made of a polymethacrylic acid derivative or a cellulose derivative, especially consisting of hydroxypropylmethylcellulosephthalate and dibutylphthalate.

The mixing ratio of CMT-Base and carrier substance can vary within broad limits within the context of the invention. In general, the minimum concentration of carrier substance is limited by the stability effect to be attained. The minimum content of carrier substance in the mixture is about 20% by weight. Below this limit, the stabilization effect is no longer adequate. The maximum share of carrier substance generally is not limited, except for orally applicable capsules. In this case, if the mixture contains more than 80% carrier substance, the total volume of the capsule becomes so great that oral applicability is doubtful.

The quantity of the mixture of CMT-Base and carrier substance, contained in a gelatin capsule as a single dose, depends on the particular case of application. Generally, quantities between 300 and 1,000 mg can be considered to be the best levels here.

The invention will be explained further with the help of the following examples.

EXAMPLE 1

A 10-liter noble-steel stirring vessel, in the vacuum design, is filled with 4.0 kg of neutral oil (Miglyol 812) and, after removal of the air, by means of the application of a vacuum (10 min, 1 mm Hg), it is gassed with industrially pure nitrogen. The nitrogen is here conducted directly into the neutral oil with the help of a distributor. During further nitrogen gassing, while stirring is continued, 4.0 kg of freshly distilled $O_2$-free CMT-Base, with a chloride content of about 0.01%, is slowly added, specifically, at 200 ml/min. The mixture is filled into stainless steel transportation containers after stirring another 10 minutes. Then the mixture is poured, free of any air bubbles, into soft gelatin capsules which will dissolve in gastric juice. The filling quantity per capsule is 500 mg of mixture.

EXAMPLE 2

A 5-liter evacuable (round-bottomed flask) glass stirring vessel is filled with 1.5 kg tricaprin (glycerin-tricaprinate) and, after removal of the air, by means of application of a vacuum (10 min, 1 mm Hg) is gassed with industrially pure argon. The argon is here conducted into the tricaprin solution by means of a distributor. During further argon gassing, while stirring continues, 1.0 kg of freshly distilled $O_2$-free CMT-Base, with a chloride content of about 0.01%, is allowed continually to drip in over a period of 10 minutes and the mixture is then poured into an argon-gassed 3-liter gas flask. Then the mixture is poured, without any air bubbles, into soft gelatin capsules which will resist gastric juice and which can be dissolved in the intestines; each of these capsules gets 600 mg of mixture.

EXAMPLE 3

A 10-liter noble steel stirring vessel, in the vacuum design, is filled with 4.0 kg tricaprylin (glycerin-tricapralate) and is further treated according to Example 1.

EXAMPLE 4

A 10-liter noble steel stirring vessel, in the vacuum design, is filled with 2.0 kg trilaurin (glycerin-trilaurate) and 2.0 kg tricaprin (glycerin-tricaprinate) and is further treated according to Example 1.

EXAMPLE 5

A 5-liter evacuable (round-bottomed flask) glass stirring vessel is filled with 1.5 kg neutral oil in the form of a triglyceride mixture of saturated fatty acids and is further treated according to Example 2.

Experiments have been conducted to provide evidence that, in addition to HCl separation, other reactions can lead to the decomposition of the CMT-Base.

The mechanism of HCl separation is given by the following formula.

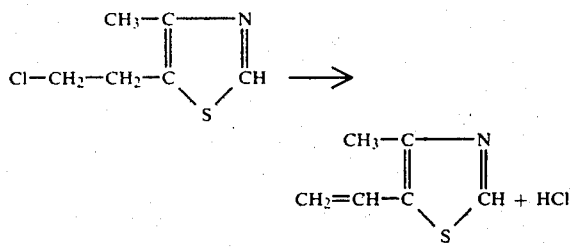

If HCl separation is the only possible cause of the decomposition of the CMT-Base, then one must not find any reaction products which contain bound chloride.

Freshly distilled Clomethiazol-Base was kept for 7 days at 70° C., and the precipitated brown deposit (decomposition products) was washed with benzene and analyzed. Determinations of the total chloride and of free-chloride, gas-chromatography determination of occluded CMT-Base+CMT-HCl and $^1$H-NMR-spectroscopic investigations, conducted on the deposit, revealed the following result.

The quantity of total chloride determined is 17% greater than the sum of free chloride and chloride of occluded CMT-Base and CMT-HCl. This 17% chloride surplus accordingly must be bound to the decomposition products of the CMT-Base. The $^1$H-NMR spectroscopic investigations of the deposit support the above result by means of the appearance of additional indications of aliphatic protons which cannot be associated with the possible decomposition products of HCl separation.

Two mixtures of CMT-Base and neutral oil were made.
Mixture I:
  83.5% by weight CMT-Base,
  16.5% by weight neutral oil
Mixture II:
  31.2% by weight CMT-Base,
  68.8% by weight neutral oil Experimental Setup 1: Mixtures I and II were heated in a glass flask at 70° C. in a nitrogen atmosphere for 100 and 170 hours and the decomposition of the CMT-Base was determined.

| | Decomposition of CMT-Base in % | |
|---|---|---|
| | 100 Hours | 170 Hours |
| Mixture I | 3.5 | 4.9 |
| Mixture II | <0.5% | <0.5% |

Experimental Setup 2: Mixtures I and II were heated in a glass flask in an air atmosphere at 70° C. for 170 hours and the decomposition of the CMT-Base was determined.

| | Decomposition of CMT-Base in % After 170 Hours |
|---|---|
| Mixture I | 14.1% |
| Mixture II | 3.7% |

A comparative consideration of the two experimental arrangements shows that the addition of neutral oil, in the form of a triglyceride mixture of saturated fatty acids, reduces the decomposition of the CMT-Base. As the neutral oil concentration increases, this stabilizer effect becomes stronger.

By excluding aerial oxygen, there is achieved a considerable increase in the stabilizing effect. This proves that aerial oxygen is significantly involved in the decomposition of the CMT-Base and that mechanisms of autoxydation are operative. If HCl separation were the only decomposition reaction taking place, then the test values obtained in an air atmosphere and a nitrogen atmosphere would have to agree.

On the basis of the excellent results of experimental arrangement 1, soft gelatin capsules (composition: 67% by weight gelatin, 19% by weight glycerin, 14% by weight sorbite) were filled with 330 mg of mixture (192 mg CMT-Base, 138 mg neutral oil), amid nitrogen washing and were stored for 16 months at 20° C., 30° C., 40° C. and 50° C. The decomposition of the CMT-Base was then determined.

The decomposition of the CMT-Base was computed in all cases through the gas-chromatography determination of the remaining undecomposed base. Compared to the approach of measuring the free chloride, this offers the advantage that possible decomposition reactions, where the chloride remains bound to the decomposition product, are considered.

Comparative determinations of the decomposition via the free chloride showed that the decomposition values, determined by means of gas-chromatography, were somewhat higher.

| | Result: |
|---|---|
| Temperature | Decomposition of CMT-Base in % |
| 20° C. | 3.1% |
| 30° C. | 8.3% |
| 40° C. | 9.6% |
| 50° C. | 22.9% |

With the values thus obtained, an advance stability computation was predicted according to the laws of chemical reaction kinetics, using the literature published in this connection. At room temperature, one can expect a lifetime of 4 years. All capsules were absolutely odor-tight after heat treatment.

The chemical stability of pharmaceutical products is a main criterion for therapeutic reliability and economical medication production as well as sale and is thus a fundamental requirement of most medical licensing authorities. The present demonstrable extension of stability consequently constitutes an essential improvement in the medication value of products of the type in question.

We claim:
1. A method for stabilizing 4-methyl-5-(2'-chloroethyl)-thiazol, comprising admixing said thiazol in the absence of oxygen with a non-toxic carrier consisting essentially of at least one triglyceride of at least one saturated fatty acid of a chain length of 8 to 12 carbon atoms which is substantially free of heavy metal ions and double bonds, the amount of said carrier being between about 20% and about 80% by weight of said thiazol.

2. The method of claim 1, wherein said triglyceride is of a mixture of said saturated fatty acid.

3. The method according to claim 1, wherein said fatty acid is a vegetable fatty acid.

4. The method of claim 1, wherein said triglyceride is glyceryl tricaprinate or glyceryl trilaurate or a mixture thereof.

5. The method of claim 1, wherein said thiazol and said carrier are admixed in a nitrogen atmosphere and this nitrogen atmosphere is maintained until the mixture is filled into gelatin capsules.

* * * * *